United States Patent [19]
Schläpfer

[11] 3,966,755
[45] June 29, 1976

[54] COUMARIN DERIVATIVES

[75] Inventor: Hans Schläpfer, Basel, Switzerland

[73] Assignee: Ciba-Geigy Corporation, Ardsley, N.Y.

[22] Filed: June 18, 1973

[21] Appl. No.: 370,880

[30] Foreign Application Priority Data
June 21, 1972 Switzerland............... 9335/72

[52] U.S. Cl................ 260/308 A; 8/1 W; 252/301.27; 252/301.29; 260/247.1 M; 260/247.2 A; 260/247.2 B; 260/293.58; 260/310 R

[51] Int. Cl.$^2$............ C07D 405/04; C07D 405/14; C07D 413/14

[58] Field of Search............... 260/308 A

[56] References Cited
UNITED STATES PATENTS

| | | |
|---|---|---|
| 3,014,041 | 12/1961 | Häusermann et al............... 260/304 |
| 3,271,412 | 9/1966 | Rawe et al............... 260/308 A |
| 3,636,004 | 1/1972 | Bode et al............... 260/308 A |
| 3,686,202 | 8/1972 | Kirchmayr et al............... 260/308 A |

*Primary Examiner*—Raymond V. Rush
*Attorney, Agent, or Firm*—Joseph G. Kolodny; Edward McC. Roberts; Prabodh I. Almaula

[57] ABSTRACT

The present invention relates to new coumarine derivatives in which coumarine residues substituted in 7-position or 5,6-benzo-coumarine residues are further substituted in 3-position by optionally further substituted 2-phenyl-triazol-4-yl 2- or 1-phenyl-pyrazol-4-yl.

The new compounds are useful optical brighteners for organic materials.

12 Claims, No Drawings

COUMARIN DERIVATIVES

The present invention relates to new coumarine derivatives, their use as optical brighteners for organic materials, and processes for their manufacture.

The new coumarin derivatives correspond to the formula (1) 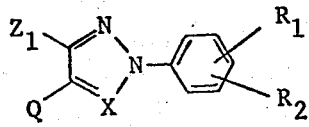

wherein $Z_1$ represents hydrogen, chlorine or methyl, $R_1$ represents hydrogen, halogen, alkyl with 1 to 4 carbon atoms, alkoxy with 1 to 4 carbon atoms or alkylsulphonyl with 1 to 4 carbon atoms, $R_2$ represents hydrogen, halogen or alkyl with 1 to 4 carbon atoms, X represents nitrogen or —CH= and Q represents a radical

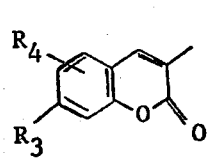 or 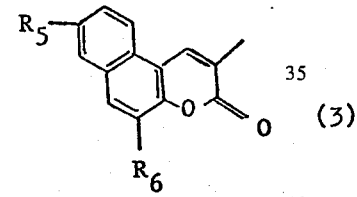

wherein $R_3$ denotes an alkoxy with 1 to 12 carbon atoms, alkenyloxy with 2 to 5 carbon atoms, benzyloxy which is optionally chlorine-substituted in the phenyl radical, acyloxy with 2 to 12 carbon atoms, benzoyloxy which is optionally substituted by chlorine, methyl or methoxy, acylamino with 2 to 12 carbon atoms, benzoylamino which is optionally substituted by chlorine, methyl or methoxy, a —NHCOOY radical, wherein y represents alkyl with 1 to 12 carbon atoms or phenyl which is optionally substituted by chlorine, methyl or methoxy, a —NHCONHY$_1$ radical, wherein $Y_1$ represents alkyl with 1 to 4 carbon atoms or phenyl which is optionally substituted by chlorine, methyl or methoxy, an optionally quaternised radical

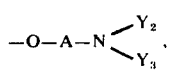

wherein A represents alkylene with 2 to 4 carbon atoms, $Y_2$ and $Y_3$ independently of one another represent optionally hydroxy-substituted alkyl with 1 to 4 carbon atoms or $Y_2$ and $Y_3$ together with the nitrogen represent pyrrolidino, piperidino or morpholino, $R_4$ denotes hydrogen, chlorine, methyl or methoxy and $R_5$ and $R_6$ independently of one another denote hydrogen, alkyl with 1 to 4 carbon atoms or carboalkoxy with 2 to 5 carbon atoms.

The formula (1) accordingly embraces the compounds of the formulae (2) 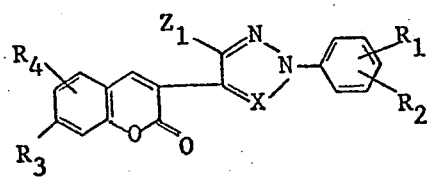

and (3) 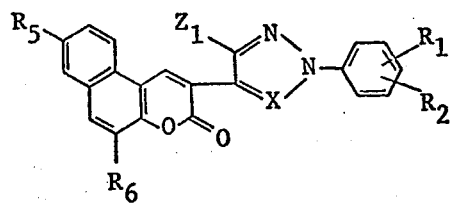

Compounds to be mentioned particularly are those of the formula (4) 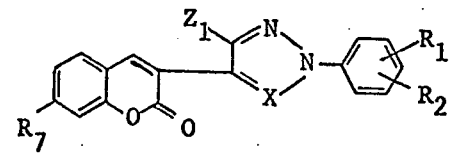

wherein $R_7$ represents alkoxy with 1 to 12 carbon atoms, alkenyloxy with 2 to 5 carbon atoms or benzyloxy which is optionally chlorine-substituted in the phenyl part, and X, $Z_1$, $R_1$ and $R_2$ have the indicated meaning.

Within the frameword of the formula (4), compounds of interest are above all those of the formula (5) 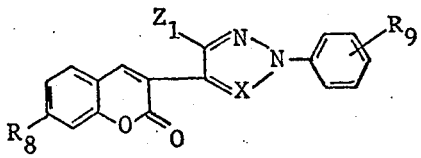

wherein $Z_1$ represents hydrogen, chlorine or methyl, $R_8$ represents alkoxy with 1 to 4 carbon atoms or benzyloxy, $R_9$ represents hydrogen, chlorine or methyl and X has the indicated meaning.

Compounds of particular practical interest correspond to the formula (6) 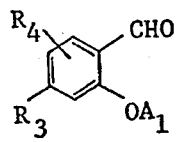

wherein $Z_2$ represents hydrogen or methyl, $R_9$ represents hydrogen, methyl or chlorine and $Q_1$ represents a radical

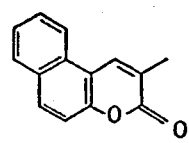 or 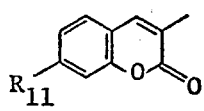

wherein $R_{11}$ represents alkoxy with 1 to 4 carbon atoms, benzyloxy, acetamido or a carbamic acid ethyl ester radical, and X has the indicated meaning.

Preferred comopunds of the formulae (1) to (6) are in each case those in which the symbol X represents nitrogen.

Further compounds which deserve particular mention are those of the formula (7) 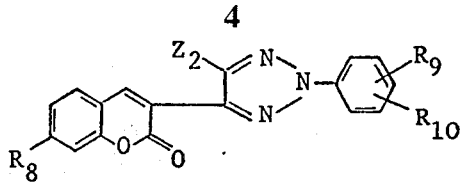

wherein $Z_2$ denotes hydrogen or methyl, $R_8$ denotes alkoxy with 1 to 4 carbon atoms or benzyloxy, $R_9$ denotes hydrogen, chlorine or methyl and $R_{10}$ denotes hydrogen, chlorine or methyl.

The compounds of the formula (1) or of subordinate formulae can be manufactured analogously to processes which are in themselves known.

Compounds according to the invention, of the formula (1), are obtained, for example, when an aldehyde of the formula (8) 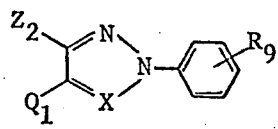

or (9) 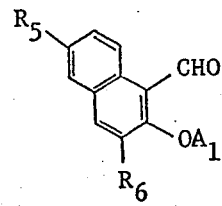

wherein $A_1$ represents hydrogen, alkyl with 1 to 4 carbon atoms or acyl with 1 to 4 carbon atoms and $R_3$, $R_4$, $R_5$ and $R_6$ have the indicated meaning, or a derivative thereof which reacts in the same way under the reaction conditions, for example an anil, is condensed under cyclisation conditions according to known methods with an acetic acid derivative of the formula

(10) 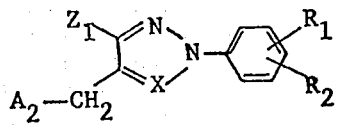

wherein $A_2$ represents a carboxyl group of its salts (such as, for example, K, Na or ammonium salts), carboalkoxy with 2 to 5 carbon atoms or the nitrile group and $Z_1$, $R_1$, $R_2$ and X have the indicated meaning.

The starting products of the formulae (8), (9) and (10) are known or can be manufactured analogously to processes which are in themselves known.

In the process for the manufacture of compounds of the formula (1), a compound of the formula

(11) 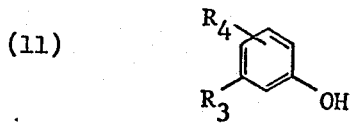

or (12) 

wherein $R_3$, $R_4$, $R_5$ and $R_6$ have the indicated meaning, is condensed, in the presence of an inert organic solvent, and, for example, of aluminum chloride, aluminum bromide, aluminum hydroxydichloride, boron trifluoride or boron fluoride ethyl ether as the condensation agent, at a temperature of 60° to 200°C, with a compound of the formula

(13) 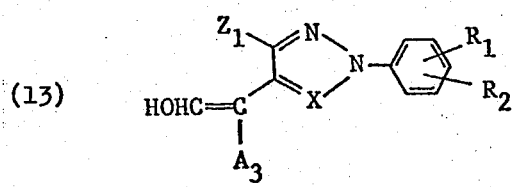

wherein $A_3$ represents the nitrile group, the carboxyl group or a carboalkoxy group with 2 to 5 carbon atoms and $Z_1$, $R_1$, $R_2$ and X have the indicated meaning.

Suitable inert organic solvents are, for example, nitrobenzene, p-nitrotoluene, M-nitrochlorobenzene and 1,1,2,2-tetrachloroethane. This process is very particularly suitable for the manufacture of those compounds of the formula (1) in which $R_3$ represents a —NHCOOY or —NHCONHY$_1$ radical, since in that case it is possible to start from a m-aminophenol in order to form appropriate derivatives of the free amino group at the end of the condensation.

The compounds of the formula (1) can furthermore be manufactured according to the Meerwein coupling reaction. Herein, a coumarin derivative of the formula

(14) 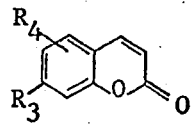

or (15) 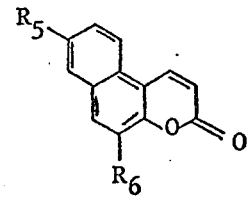

wherein $R_3$, $R_4$, $R_5$ and $R_6$ have the indicated meaning, is reacted with a diazonium salt of the formula

(16) 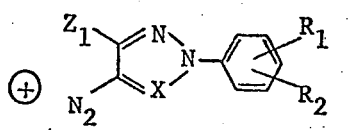

wherein $R_1$, $R_2$, $Z_1$ and X have the indicated meaning. The reaction is generally carried out in an aqueous or aqueous-organic phase, such as water-acetone, water-methanol or water-ethanol and the like, at temperatures of −10° to 60°C, preferably at 20° to 40°C, and in the presence of copper salts, optionally in the presence of a buffer which is effective in the acid range, for example acetic acid-sodium acetate, monosodium triphosphate, monosodium tartrate and the like.

The compounds of the formulae (11) to (16) are known or can be manufactured analogously to known processes.

The new compounds defined above show a more or less pronounced fluorescense in the dissolved or finely divided state. They can be used for the optical brightening of the most diverse synthetic, semi-synthetic or natural organic materials or substances which contain such organic materials.

The following groups of organic materials, where optical brightening thereof is relevant, may be mentioned as examples of the above, without the survey given below being intended to express any restriction thereto:

I. Synthetic organic high molecular materials:

a. Polymerisation products based on organic compounds containing at least one polymerisable carbon-carbon double bond, that is to say their homopolymers or copolymers as well as their after-treatment products such as, for example, crosslinking, grafting or degradation products, polymer blends or products obtained by modification or reactive groups, for example polymers based on $\alpha,\beta$-unsaturated carboxylic acids or derivatives of such carboxylic acids, especially on acrylic compounds (such as, for example, acrylic esters, acrylic acid, acrylonitrile, acrylamides and their derivatives or their methacryl analogues), on olefine hydrocarbons (such as, for example, ethylene, propylene, styrenes or dienes and also so-called ABS polymers), and polymers based on vinyl and vinylidene compounds (such as, for example, vinyl chloride, vinyl alcohol and vinylidene chloride), b. Polymerisation products such as are obtainable by ring opening, for example, polyamides of the polycarprolactam type, and also polymers which are obtainable both via polyaddition and via polycondensation, such as polyethers or polyacetals.

c. Polycondensation products or precondensates based on bifunctional or polyfunctional compounds possessing condensable groups, their homocondensation and co-condensation products, and after-treatment products, such as, for example, polyesters, especially saturated (for example ethylene glycol terephthalic acid polyester) or unsaturated (for example maleic acid-dialcohol polycondensates as well as their crosslinking products with copolymerisable vinyl monomers), unbranched and branched (also including those based on polyhydric alcohols, such as, for example alkyd resins) polyesters, polyamides (for example hexamethylenediamine adipate), maleate resins, maleamine resins, their precondensates and analogous polycarbonates and silicones, d. Polyaddition products such as polyurethanes (crosslinked and non-crosslinked) and epoxide resins.

II. Semi-synthetic organic materials, for example, cellulose esters of varying degrees of esterification (so-called 2½-acetate or triacetate) or cellulose ethers, regenerated cellulose (viscose or cuprammonium cellulose), or their after-treatment products, and casein plastics.

III. Natural organic materials of animal or vegetable origin, for example based on proteins, such as wool, silk, natural lacquer resins, starch and casein.

The organic materials to be optically brightened can be in the most diverse states of processing (raw materials, semi-finished goods or finished goods). On the other hand, they can be in the form of structures of the most diverse shapes, say for example predominantly three-dimensional bodies such as sheets, profiles, injection mouldings, various machined articles, chips, granules or foams, and also as predominantly two-dimensional bodies such as films, foils, lacquers, coverings, impregnations and coatings, or as predominantly one-dimensional bodies such as filaments, fibres, flocks and wires. The said materials can, on the other hand, also be in an unshaped state, in the most diverse homogeneous or inhomogeneous forms of division, such as, for example, in the form of powders, solutions, emulsions, dispersions, latices, pastes or waxes.

Fibre materials can, for example, be in the form of endless filaments (stretched or unstretched), staple fibres, flocks, hanks, textile filaments, yarns, threads, fibre fleeces, felts, waddings, flocked structures or woven textile fabrics, textile laminates, knitted fabrics and papers, cardboard or paper compositions.

The compounds to be used according to the invention are of importance, inter alia, for the treatment or organic textile materials, especially woven textile fabrics. Where fibres, which can be in the form of stape fibres or endless filaments or in the form of hanks, woven fabrics, knitted fabrics, fleeces, flocked substrates or laminates, are to be optically brightened according to the invention, this is advantageously effected in an aqueous medium, wherein the compounds in question are present in a finely divided form (suspensions, so-called microdispersions or possibly solutions). If desired, dispersing agents, stabilisers, wetting agents and further auxiliaries can be added during the treatment.

Depending on the type of brightener compound used, it may prove advantageous to carry out the treatment in a neutral or alkaline or acid bath. The treatment is usually carried out at temperatures of about 20° to 140°C, for example at the boiling point of the bath or near (about 90°C). Solutions or emulsions in organic solvents can also be used for the finishing, according to the invention, of textile substrates, as is practised in the dyeing trade in so-called solvent dyeing (pad-thermofix application, or exhaustion dyeing process in dyeing machines).

The new optical brighteners according to the present invention can further be added to, or incorporated in, the materials before or during their shaping. Thus they can, for example, be added to the compression moulding composition or injection moulding composition during the manufacture of films, sheets (for example, hot milling into polyvinyl chloride) or mouldings.

Where fully synthetic or semi-synthetic organic materials are being shaped by spinning processes or via spinning compositions, the optical brighteners can be applied in accordance with the following processes:

addition to the starting substances (for example monomers) or intermediates (for example precondensates or prepolymers), that is to say before or during the polymerisation, polycondensation or polyaddition, powdering onto polymer chips or granules for spinning compositions, bath dyeing of polymer chips or granules for spinning compositions, metered addition to spinning melts or spinning solutions, and application to the two before stretching.

The new optical brighteners according to the present invention can, for example, also be employed in the following use forms:

a. Mixed with dyestuffs (shading) or pigments (coloured pigments or especially, for example, white pigments), or as an additive to the dye baths, printing pastes, discharge pastes or reserve pastes, or for the after-treatment of dyeings, prints or discharge prints.

b. Mixed with so-called "carriers", wetting agents, plasticisers, swelling agents, anti-oxidants, light protection agents, heat stabilisers and chemical bleaching agents (chlorite bleach or bleaching bath additives).

c. Mixed with crosslinking agents or finishing agents (for example starch or synthetic finishes), and in combination with the most diverse textile finishing processes, especially synthetic resin finishes (for example creaseproof finishes such as "wash-and-wear", "permanent-press" or "no-iron"), as well as flameproof finishes, soft handle finishes, anti-soiling finishes or anti-static finishes, or antimicrobial finishes.

d. Incorporation of the optical brighteners into polymeric carriers (polymerisation, polycondensation or polyaddition products), in a dissolved or dispersed form, for use, for example, in coating agents, impregnating agents or binders (solutions, dispersions and emulsions) for textiles, fleeces, paper and leather.

e. As additives to so-called "master batches".

f. As additives to the most diverse industrial products in order to render these more marketable (for example improving the appearance of soaps, detergents, pigments), g. In combination with other optically brightening substances, h. In spinning bath preparations, that is to say as additives to spinning baths such as are used for improving the slip for the further processing of synthetic fibres, or from a special bath before the stretching of the fibre.

i. As scintillators for various purposes of a photographic nature, such as, for example, for electrophotographic reproduction for the optical brightening of photographic layers, optionally in combination with white pigments such as, for example $TiO_2$ or supersensitisation.

If the brightening process is combined with textile treatment methods or finishing methods, the combined treatment can in many cases advantageously be carried out with the aid of appropriate stable preparations, which contain the optically brightening compounds in such concentration that the desired brightening effect is achieved.

In certain cases, the brighteners are made fully effective by an after-treatment. This can, for example, represent a chemical treatment (for example acid treatment), a thermal treatment (for example heat) or a combined chemical/thermal treatment. Thus, for example, the appropriate procedure to follow in optically brightening a series of fibre substrates, for example of polyester fibres, with the brighteners according to the invention is to impregnate these fibres with the aqueous dispersions (or optionally also solutions) of teh brighteners at temperatures below 75°C, for example at room temperature, and to subject them to a dry heat treatment at temperatures above 100°C, it being generally advisable additionally to dry the fibre material beforehand at a moderately elevated temperature, for example at not less than 60°C and up to about 130°C. The heat treatment in the dry state is then advantageously carried out at temperatures between 120° and 255°C, for example by heating in a drying chamber, by ironing within the specified temperature range or by treatment with dry, superheated steam. The drying and dry heat treatment can also be carried out in immediate succession or be combined in a single process stage.

The amount of the new optical brighteners to be used according to the invention, relative to the material to be optically brightened, can vary within wide limits. A distinct and durable effect is already achievable with very small amounts, in certain cases, for example, amounts of 0.0001 percent by weight. However, amounts of up to about 0.8 percent by weight and optionally of up to about 2 percent by weight can also be employed. For most practical purposes, amounts between 0.0005 and 0.5 percent by weight are of preferred interest.

The new optical brightening agents are also particularly suitable for use as additives for wash liquors or industrial and domestic washing agents, to which they can be added in various ways. They are appropriately added to wash liquors in the form of their solutions in water or organic solvents or in a finely divided form, as aqueous dispersions. They are advantageously added to domestic or industrial washing agents in any stage of the manufacturing process of the washing agents, for example to the so-called "slurry" before spray-drying, to the washing powder, or during the preparation of liquid washing agent combinations. They can be added either in the form of a solution or dispersion in water or other solvents or, without auxiliaries, as a dry brightening powder. For example, the brightening agents can be mixed, kneaded or ground with the detergent substances and, in this form, admixed to the finished washing powder. However, they can also be sprayed in a dissolved or pre-dispersed form onto the finished washing agent.

Possible washing agents are the known mixtures of detergent substances such as, for example, soap in the form of chips and powders, synthetics, soluble salts of sulphonic acid half esters of higher fatty alcohols, arylsulphonic acids with higher and/or multiple alkyl substituents, sulphocarboxylic acid esters of medium to higher alcohols, fatty acid acylaminoalkyl-or acylaminoaryl-glycerinesulphonates, phosphoric acid esters of fatty alcohols and the like. Possible so-called "builders" which can be used are, for example, alkali metal polyphosphates and polymetaphosphates, alkali metal pyrophosphates, alkali metal salts of carboxymethylcellulose and other "soil redeposition inhibitors", and also alkali metal silicates, alkali metal carbonates, alkali metal borates, alkali metal perborates, nitrilotriacetic acid, ethylenediaminotetraacetic acid, and foam stabilisers such as alkanolamides of higher fatty acids. The washing agents can further contain for example: antistatic agents, skin protection agents which restore fat, such as lanolin, enzymes, antimicrobial agents, perfumes and dyestuffs.

The new optical brighteners have the particular advantage that they are also active in the presence of active chlorine donors such as, for example, hypochlorite, and can be used without significant loss of the effects in wash liquors containing non-ionic washing agents, for example alkylphenol polyglycol ethers.

The compounds according to the invention are added in amounts of 0.005–1% or more, relative to the weight of the liquid or pulverulent finished washing agent. Wash liquors which contain the indicated amounts of the optical brighteners claimed impart a brilliant appearance in daylight when used to wash textiles of polyamide fibres, cellulose fibres with a high quality finish, polyester fibres, wool and the like.

The washing treatment is carried out as follows, for example:

The textiles indicated are teated for 1 to 30 minutes at 20° to 100°C in a wash liquor which contains 1 to 10 g/kg of a built-up composite washing agent and 0.05 to 1%, relative to the weight of the washing agent, of the claimed brightening agents. The liquor ratio can be 1:3 to 1:50. After washing, the textiles are rinsed and dried in the usual manner. The wash liquor can contain 0.2 g/l of active chlorine (for example as hypochlorite) or 0.1 to 2 g/l of sodium perborate as a bleaching additive.

In the examples the parts, unless otherwise stated are always parts by weight and the percentages are always percentages by weight. Unless otherwise noted, melting points and boiling points are uncorrected.

EXAMPLE 1

9.9 g of 2-hydroxy-4-methoxybenzaldehyde are introduced into a mixture of 15.5 g of the sodium salt of 5-methyl-2-phenyl-v-triazolyl-4-acetic acid and 130 ml of acetic anhydride. The reaction mixture is heated to the boil over the course of 1 hour and is boiled under reflux for 7½ hours. After the reaction mixture has cooled to approx. 80°C, it is poured out onto approx. 1,700 ml of water and after the excess acetic anhydride has hydrolysed, the reaction product is filtered off, washed with water until neutral and subsequently stirred with a little alcohol to form a paste, and the crystalline material is filtered off and again washed with alcohol. After two recrystallisations from chlorobenzene with the aid of fuller's earth, about 7 g of the compound of the formula

(17) 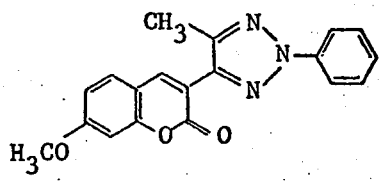

are obtained as colourless, felted small crystal needles of melting point 216° to 216.5°C.

If instead of 2-hydroxy-4-methoxybenzaldehyde an equivalent amount of 2-hydroxy-4-isopropoxybenzaldehyde is used and in other respects the procedure described in the example is followed, the compound of the formula

(18) 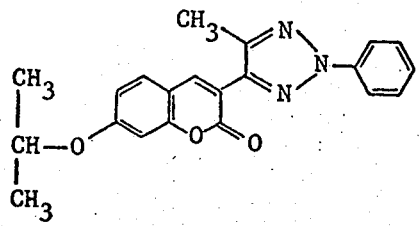

is obtained, which after recrystallisation from isopropanol is obtained in almost colourless crystals of melting point 138° to 139°C.

If instead of the sodium salt of 5-methyl-2-phenyl-v-triazolyl-4-acetic acid an equivalent amount of the sodium salt of 2-phenyl-v-triazolyl-4-acetic acid is used and in other respects the procedure described in the example is followed, the compound of the formula

(19) 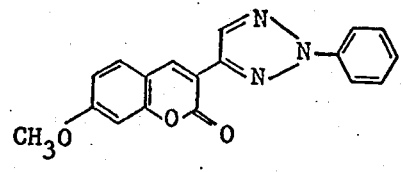

is obtained, after recrystallisation from chlorobenzene, as pale yellow-greenish-tinged small crystal needles of melting point 196° to 196.5°C.

Analogously, 2-hydroxy-4-n-butoxybenzaldehyde or 2-hydroxy-4-benzyloxybenzaldehyde and the sodium salt of 2-phenyl-v-triazolyl-4-acetic acid respectively yield the compound of the formula

(20) 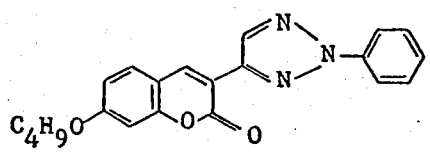

which after recrystallisation from toluene is in the form of hair-fine, felted, colourless small needles of melting point 161° to 161.5°C, or fo the formula

(21) 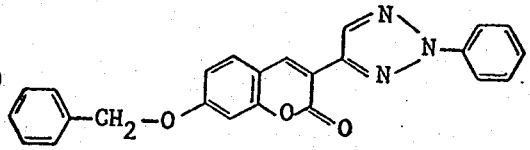

which after recrystallisation from chlorobenzene is in the form of pale yellow-greenish-tinged small crystals of melting point 219° to 220.5°C.

EXAMPLE 2

7.6 g of 2-hydroxy-4-methoxybenzaldehyde are introduced into a mixture of 13.0 g of the sodium salt of 2-m-chlorophenyl-v-triazolyl-4-acetic acid and 100 ml of acetic anhydride. The reaction mixture is brought to the boil over the course of 1 hour and is boiled under reflux for 6½ hours. After cooling, the mixture is poured out into a large amount of water and after the excess acetic anhydride has hydrolysed the reaction product is separated off, washed with water and dried. After a preliminary purification by recrystallisation from 270 ml of toluene, 9 g of pre-purified product are obtained. After two recrystallisations from toluene with the aid of fuller's earth, the compound of the formula

(22) 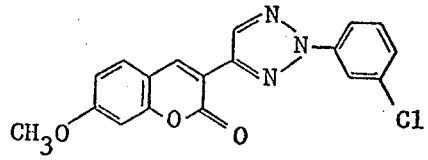

is obtained, in a yield of 7.4 g, in the form of pale yellow-greenish-tinged fine crystals of melting point 202° to 202°C.

If instead of 13 g of the sodium salt of 2-m-chlorophenyl-v-triazolyl-4-acetic acid, 13.7 g of the sodium salt of 2-(4-methyl-3-chlorophenyl)-v-triazolyl-4-acetic acid or 12 g of the sodium salt of 2-p-methylphenyl-v-triazolyl-4-acetic acid are used and in other respects the procedure described in the example is followed, the compound of the formula

(23) 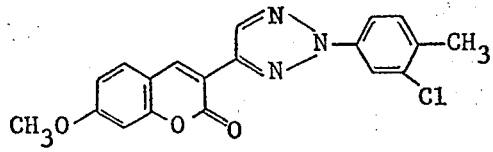

in the form of pale greenish-tinged yellow small crystal needles of melting point 241.5 to 242°C after recrystallisation from chlorobenzene, and of the formula

(24) 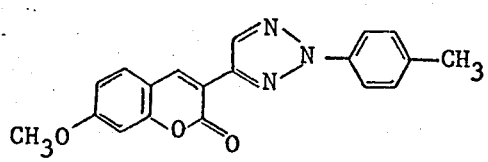

in the form of brilliant light yellow crystals of melting point 202.5° to 203°C, after recrystallisation from toluene, are respectively obtained.

The substituted 2-phenyl-v-triazolyl-4-acetic acids used as starting materials in the examples are obtained as follows:

30.5 g of 4-hydroxymethyl-2-m-chlorophenyl-v-triazole are suspended in 230 ml of 48% strength hydrobromic acid whilst stirring and thereafter the mixture is boiled under reflux for 1 hour (approx. 125°C boiling temperature). After cooling, the 4-bromomethyl-2-m-chlorophenyl-v-triazole which has crystallised, is filtered off, washed with water and dried. Yield: 39.6 g (100%), crude melting point: 58° to 60°C. A sample recrystallised from hexane melts at 60° to 61°C.

39.6 g of crude 4-bromomethyl-2-m-chlorophenyl-v-triazole are added, at room temperature, to a solution of 11.5 g of potassium cyanide in 11.6 ml of water and 53 ml of 95% strength ethanol. The suspension is thereafter warmed to 55°C, in the course of which the moderately exothermic reaction starts. The source of heat is advantageously removed for a short time. After the exothermic reaction has subsided, the mixture is additionally boiled for 3 hours under reflux and then poured out onto 500 ml of water, and the crystalline 4-cyanomethyl-2-m-chlorophenyl-v-triazole is filtered off, washed with water and dried. Yield: 31.3 g (98%). Crude melting point: 88° to 93°C. A sample recrystallised from hexane melts at 92° to 93°C.

31.3 g of crude 4-cyanomethyl-2-m-chlorophenyl-v-triazole are saponified by boiling for 3 hours under reflux with a solution of 92 g of sodium hydroxide in 1,000 ml of water, the slightly cloudy reaction solution is clarified by filtering it hot and thereafter 202 ml of 37.3% strength hydrochloric acid are slowly added at 50° to 60°C (pH approx. 3), in the course of which 2-m-chlorophenyl-v-triazolyl-4-acetic acid separates out as a colourless product. After cooling, filtration, washing with water and drying, 32.1 g (94%) of crude 2-m-chlorophenyl-v-triazolyl-4-acetic acid of melting point 134° to 136°C are obtained. A sample recrystallised from ethyl acetate melts at 139° to 140°C.

Analogously, 4-hydroxymethyl-2-p-methylphenyl-v-triazole and 4-hydroxymethyl-2-(4-methyl-3-chlorophenyl)-v-triazole respectively yield 2-p-methylphenyl-v-triazolyl-4-acetic acid of melting point 115° to 116°C and 2-(4-methyl-3-chlorophenyl)-v-triazolyl-4-acetic acid of melting point 144° to 145°C.

EXAMPLE 3

10.3 g of 2-hydroxy-1-naphthaldehyde are introduced into a mixture of 13.5 g of the sodium salt of 2-phenyl-v-triazolyl-4-acetic acid and 135 ml of acetic anhydride. The reaction mixture is heated to the boil over the course of 1 hour, whilst stirring, and is boiled under reflux for 5½ hours. After the reaction mixture has cooled to approx. 80°C, it is poured out onto approx. 1,700 ml of cold water and after several hours the product is filtered off, washed with water and dried in vacuo at 60° to 70°C. After a preliminary purification by recrystallisation from 235 ml of chlorobenzene, 11.05 g of pre-purified product (54.5% of theory) are obtained. After two recrystallisations from chlorobenzene with the aid of fuller's earth, the compound of the formula

(25) 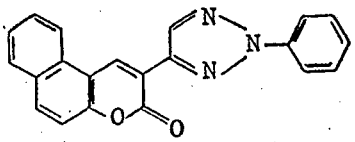

is obtained in a yield of 8.5 g, as luminous yellow crystal flakes of melting point 238° to 238.5°C.

If instead of 13.5 g of the sodium salt of 2-phenyl-v-triazolyl-4-acetic acid, 14.4 g of the sodium salt of 5-methyl-2-phenyl-v-triazolyl-4-acetic acid are used and in other respects the procedure described in the example is followed, the compound of the formula

(26) 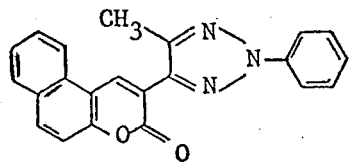

is obtained from chlorobenzene as pale yellow felted small crystal needles of melting point 274.5° to 275°C.

EXAMPLE 4

18.4 g of 1-phenylpyrazolyl-4-acetonitrile and 16.6 g of 2,4-dimethoxybenzaldehyde are dissolved in 80 ml of methanol at 25° to 30°C. 1.5 ml of 50% strength potassium hydroxide solution are then added, the reaction mixture is stirred for 3 hours at room temperature and subsequently for 3 hours at 50° to 55°C and is cooled, after stirring for a further hour at room temperature, to 0°–5°C, and after 2–3 hours the yellow methine compound is filtered off and washed twice with cold methanol and then with water, and the product is dried in vacue at 60°C. 22.1 g of crude α-(1-phenylpyrazolyl-4)-β-(2,4-dimethoxyphenyl)-acrylonitrile are obtained. When recrystallised from benzene/ligroin, the compound melts at 135°–137°C.

16.6 g of crude methine compound are introduced into 150 ml of benzene whilst stirring, 27 g of anhydrous aluminium chloride are added and the reaction mixture is heated to the boil for 6 hours, under a reflux condenser. Thereafter it is cooled, 275 ml of ice water and 35 ml of 30% strength hydrochloric acid are added and the solvent is distilled off in steam. The solid distillation residue which remains is filtered off, washed with dilute hydrochloric acid and subsequently with water until free of acid, and dried. 15.3 g of crude 3-(1-phenylpyrazolyl-4)-7-hydroxycoumarin, melting point 262°–265°C, are obtained. A sample recrystallised from alcohol melts at 265°–267°C.

12.15 g of the 7-hydroxycoumarin manufactured above are dissolved in 1,000 ml of ethanol at 70° to 75°C, whilst stirring. 36.8 ml of 15% strength potassium carbonate solution are then slowly added dropwise. After addition of 16.0 g of n-butyl bromide, the reaction mixture is stirred for 20 hours at 70° to 75°C, 8 g of n-butyl bromide and 8 ml of 15% strength potassium carbonate solution are added, and the mixture is stirred for a further 18 hours at the same temperature. After cooling, the crystals which have separated out are dried. After a recrystallisation from chlorobenzene, with the aid of fuller's earth, 9.5 g of the compound of the formula (27)

are obtained as light yellow-green crystals of melting point 207° to 208°C.

The coumarins of the formula (28)

can be manufactured analogously from 2,4-dimethoxybenzaldehyde and the appropriate 1-phenylpyrazolyl-4-acetonitriles, with subsequent alkylation with dimethyl sulphate or aralkylation with benzyl chloride.

| Formulae | V | $V_1$ | Melting point, °C |
|---|---|---|---|
| (29) | $CH_3-$ | H | 250 to 251 |
| (30) | ⌬$CH_2-$ | H | 246 to 247 |
| (31) | $CH_3-$ | 4-$CH_3$ | 246 to 247 |
| (32) | $CH_3-$ | 3-Cl | 259 to 260 |
| (33) | $CH_3-$ | 4-Cl | 273 to 275 |

The 1-phenylpyrazolyl-4-acetonitriles used as starting materials are obtained as follows:

25.3 g of 1-phenylpyrazole, 8.5 g of paraformaldehyde and 2.35 g of anhydrous zinc chloride are suspended in 250 ml of ligroin, whilst stirring. After adding 2 drops of concentrated sulphuric acid, the reaction mixture is brought to the boil under reflux and dry hydrochloric acid gas is passed in over the course of 1½ hours. The clear ligroin solution is then decanted from the viscous phase whilst still warm and the oily constituents are extracted by boiling 10 times with 40 ml of benzene. The combined extracts are briefly washed with cold sodium bicarbonate solution, dried with sodium sulphate and filtered, and the solvent is removed in vacuo on a water bath. 19.4 g of crude 4-chloromethyl-1-phenylpyrazole are obtained as a cream-coloured crystalline product.

21.0 g of crude 4-chloromethyl-1-phenylpyrazole are dissolved in 100 ml of acetone at room temperature and after adding 6.0 g of sodium cyanide and 0.2 g of potassium iodide the mixture is heated to the boil under reflux for 24 hours, whilst stirring. After cooling, inorganic salts are filtered off and rinsed with acetone, and the solvent is distilled off. The residual oil is thereafter dissolved in 300 ml of ether and extracted by shaking with 50 ml of cold water and subsequently with saturated sodium chloride solution, the organic phase is dried with sodium sulphate and after filtration the solvent is removed. 18.4 g of crude 1-phenylpyrazolyl-4-acetonitrile are obtained as a brown oil which can be used without further purification.

The corresponding substituted 1-phenylpyrazolyl-4-acetonitriles can be manufactured analogously from 1-p-toluylpyrazole, 1-(3-chlorophenyl)-pyrazole and 1-(4-chlorophenyl)-pyrazole.

EXAMPLE 5

12.9 g of 2-phenyl-v-triazolyl-4-acetonitrile and 13.5 g of 2-methoxy-4-acetylamino-benzaldehyde are dissolved in 200 ml of methanol by gentle warming to 35°C. 2 ml of 33% strength potassium hydroxide solution are added thereto, whilst stirring, whereupon the yellow methine compound rapidly separates out, with a slight rise in temperature. After the exothermic reaction has subsided, the reaction mixture is brought to the boil under reflux for 10 minutes and after 14 hours a crystalline product is filtered off, twice rinsed with 15 ml of methanol and dried in vacuo at 60°C. 23.0 g of α-(2-phenyl-v-triazolyl-4)-β-(2-methoxy-4-acetylaminophenyl)-acrylonitrile are obtained. After recrystallisation from methylcellosolve, a sample melts at 242°–245°C.

22.6 g of the above methine compound are suspended in 375 ml of dry benzene whilst stirring, and 42 g of anhydrous aluminium chloride are added. Thereafter the mixture is heated to the boil for 6 hours under a reflux condenser, whereupon an initially oily red-brown complex compound separates out in the course of the reaction and finally changes into an olive-green solid mass. After cooling, the complex compound is decomposed with water and hydrochloric acid, the solvent is distilled off in steam and the green-yellow residue is filtered off, washed with 0.5 N hydrochloric acid and subsequently with water and dried. Yield: 21.1 g of reaction product.

21.1 g of the above reaction product are suspended in 525 ml of ethylene glycol monomethyl ether whilst stirring and 52.5 ml of 37.2% strength hydrochloric acid are added. The reaction mixture is heated for 1½ hours to gentle boiling under reflux (about 105°C), and after cooling, 4,000 ml of water, containing 100 ml of 25% strength ammonia, are added. After 2 hours a product is filtered off, washed with water and dried in vacuo at 70° to 80°C. 17.1 g (80.5% of theory) of 3-(2-phenyl-v-triazolyl-4)-7-aminocoumarin of the formula (34)

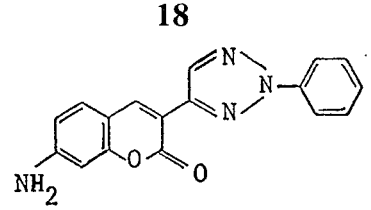

are obtained as a light yellow crystalline powder. After recrystallisation from chlorobenzene, yellow crystal flakes are obtained, which melt at 288° to 289°C.

To manufacture the acetylamino compound, 6.0 g of the aminocoumarin manufactured above are dissolved in a warm mixture of 50 ml of pyridine and 50 ml of dimethylformamide and 10 ml of acetic anhydride are then added dropwise at 75°C, whilst stirring. The reaction mixture is stirred for 1 hour at 92° to 97°C. After cooling, the fine crystalline product is filtered off, washed twice with a little pyridine and subsequently with water, and then dried. After recrystallisation from dimethylformamide, 5.7 g of the compound of the formula (35)

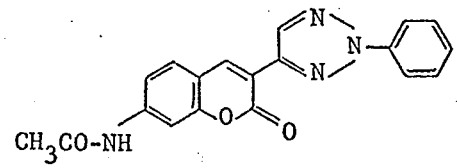

are obtained in the form of light yellow crystal needles of melting point 313° to 315°C.

If instead of 2-phenyl-v-triazolyl-4-acetonitrile an equivalent amount of 5-methyl-2-phenyl-v-triazolyl-4-acetonitrile or 1-phenylpyrazolyl-4-acetonitrile is used and in other respects the procedure described in the example is followed, the compounds of the formulae (36)

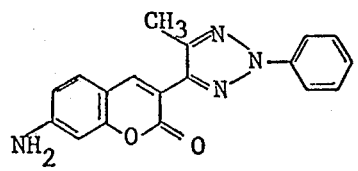

Melting point:

312 to 314°C and

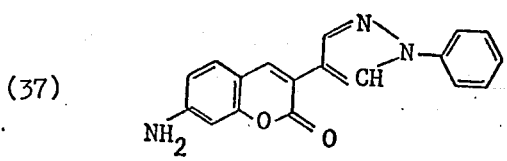

(37)

Melting point:
275 to 276°C are respectively obtained, via the stage of the methine compounds which melt at 257° to 258°C and 207° to 208°C respectively.

The urethane of the formula

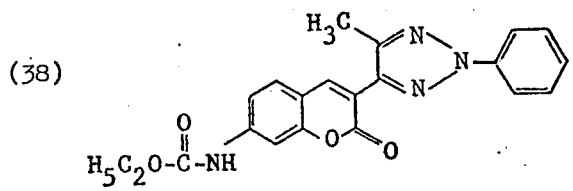

(38)

is manufactured from the compound of the formula (36). Melting point 259° to 260°C, with decomposition.

The acetyl derivative of the formula

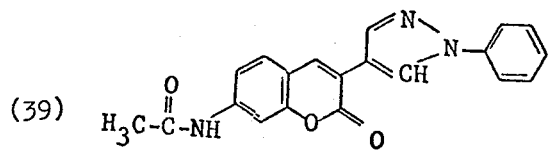

(39)

is obtained from the compound of the formula (37). Melting point: 312° to 313°C.

EXAMPLE 6

0.12 ml of 85% strength formic acid and 0.06 g of octadecyl polyglycol ether are added to 100 ml of water.

A solution of an optical brightener of the formulae (17) to (27), (29) to (33), (35), (38) or (39) is prepared by dissolving 1 g in 1,000 ml of dimethylformamide. 3 ml of this stock solution are added to the solution described above. This aqueous solution or dispersion containing the brightener is warmed to 60°C and a polyamide fabric weighing 3 g is then introduced into the solution. The temperature is raised to 92° – 95°C over the course of 10 to 15 minutes and is left thereat for 30 minutes. The fabric is then rinsed for 2 minutes in running cold water and is subsequently dried for 20 minutes at 60°C.

The fabric treated in this way shows a distinct brightening effect.

EXAMPLE 7

0.06 g of octadecyl polyglycol ether is added to 100 ml of water.

A solution of an optical brightener of the formulae (17) to (27), (29) to (33), (35), (38) or (39) is prepared by dissolving 1 g in 1,000 ml of dimethylformamide. 3 ml of this stock solution are added to the solution described above. This aqueous solution or dispersion containing the brightener is warmed to 60°C and a nylon fabric weighing 3 g is then introduced into the solution. The temperature is raised to 92° – 95°C over the course of 10 to 15 minutes and is left thereat for 30 minutes. The fabric is then rinsed for 2 minutes in running cold water and is subsequently dried for 20 minutes at 60°C.

The fabric treated in this way shows a distinct brightening effect.

EXAMPLE 8

0.4 g of a washing agent of the following composition is added to 100 ml of water:

| | |
|---|---|
| Dodecylbenzenesulphonate | 16 % |
| Fatty alcohol sulphate | 4 % |
| Na tripolyphosphate | 35 % |
| Tetra-Na pyrophosphate | 7 % |
| Mg silicate (MgSiO$_3$) | 2 % |
| Na disilicate (Na$_2$(SiO$_3$)$_2$) | 7 % |
| Carboxymethylcellulose | 1 % |
| Ethylenediaminetetraacetic acid (Na salt) | 0.5% |
| Sodium sulphate | approx. 25 % |
| Water | 2.5% |

*(Instead of sodium sulphate, the washing agent can also contain 10 to 20% of Na perborate or another oxygen-donating agent).

A solution of the optical brightener of the formula (17) to (27), (29) to (33), (35), (38) or (39) is prepared by dissolving 1 g in 1,000 ml of dimethylformamide. 2 ml of this stock solution are added to the solution described above. This aqueous solution (or dispersion) containing the brightener is warmed to 60°C. A nylon fabric weighing 3 g is then introduced into the solution and treated at this temperature for 30 minutes. The fabric is then rinsed for 2 minutes in running cold water and is subsequently dried for 20 minutes at 60°C.

The fabric treated in this way shows a distinct brightening effect.

EXAMPLE 9

0.2 g of trichlorobenzene is added to 100 ml of water.

A solution of the optical brightener of the formulae (17) to (27), (29) to (33), (35), (38) or (39) is prepared by dissolving 1 g in 1,000 ml of dimethylformamide. 1.5 ml of this stock solution are added to the solution described above. This aqueous solution containing the brightener is warmed to 60°C and a polyester fabric weighing 3 g is then introduced into the solution. The temperature is raised to 95° – 98°C over the course of 10 to 15 minutes and is left thereat for 1 hour. The fabric is then rinsed for 2 minutes in running cold water and is subsequently dried for 20 minutes at 60°C.

The fabric treated in this way shows a distinct brightening effect.

EXAMPLE 10

0.4 g of washing agent of the following composition is added to 100 ml of water:

| | |
|---|---|
| Dodecylbenzenesulphonate | 16 % |
| Fatty alcohol sulphate | 4 % |
| Na tripolyphosphate | 35 % |
| Tetra-Na pyrophosphate | 7 % |
| Mg silicate (MgSiO$_3$) | 2 % |
| Na disilicate (Na$_2$(SiO$_3$)$_2$) | 7 % |
| Carboxymethylcellulose | 1 % |
| Ethylenediaminetetraacetic acid (Na salt) | 0.5% |
| Sodium sulphate* | approx. 25 % |
| Water | 2.5% |

*(Instead of sodium sulphaate, the washing agent can also contain 10 to 20% of Na perborate or another oxygen-donating agent).

A solution of the optical brightener of the formulae (17) to (27), (29) to (33), (35), (38) or (39) is prepared by dissolving 1 g in 1,000 ml of dimethylformamide. 0.8 ml of this stock solution are added to the solution described above. This aqueous solution (or dispersion) containing the brightener is warmed to 60°C. A polyester fabric weighing 3 g is then introduced into the solution and treated at this temperature for 30 minutes. The fabric is then rinsed for 2 minutes in running cold water and is subsequently dried for 20 minutes at 60°C.

The material treated in this way shows a brightening effect which is recognisable through a corresponding fluorescence number.

EXAMPLE 11

A polyester fabric (for example "Dacron") is padded with an aqueous dispersion which contains, per litre, 2 g of a compound of the formula (17) and 1 g of an addition product of about 8 mols of ethylene oxide to 1 mol of p-tert.-octylphenol, and is dried at about 100°C. The dry material is subsequently subjected to a heat treatment at 150° to 220°C which lasts between 2 minutes and a few seconds, depending on the temperature. The material treated in this way has a substantially whiter appearance than the untreated material.

The compounds of the formulae (18) to (27), (29) to (33), (35), (38) or (39) can be used entirely analogously to achieve a similar effect.

EXAMPLE 12

0.06 ml of 40% strength acetic acid and 0.06 ml of octadecyl polyglycol ether are added to 95 ml of water.

A solution of an optical brightener of the formula (17) to (27), (29) to (33), (35), (38) or (39) is prepared by dissolving 1 g in 1,000 ml of dimethylformamide. 6 ml of this stock solution are added to the solution described above. This aqueous solution or dispersion, containing the brightener, is warmed to 40°C and an acetate fabric weighing 3 g is then introduced into the solution. The temperature is raised to 75° – 80°C over the course of 10 to 15 minutes and is kept thereat for 30 minutes. The fabric is then rinsed for 2 minutes in running cold water and is subsequently dried for 20 minutes at 60°C.

The fabric treated in this way shows a distinct brightening effect.

EXAMPLE 13

100 parts of polyester granules of terephthalic acid ethylene glycol polyester are intimately mixed with 0.05 part of a compound of the formulae (17) to (27), (29) to (33), (35), (38) or (39) in a tumbler vessel. The mixture is fused at 285°C whilst stirring, and is spun through customary spinnerets. Strongly brightened polyester fibres are obtained. The compound mentioned can also be added already before or during the polycondensation to give the polyester.

EXAMPLE 14

10,000 parts of a polyamide manufactured from $\epsilon$-caprolactam in a known manner, in the form of chips, are mixed with 30 parts of titanium dioxide (rutile modification) and 2 parts of the compound of the formula (17) to (27), (29) to (33), (35), (38) or (39) for 12 hours in a tumbler vessel. The chips treated in this way are fused, after displacing the atmospheric oxygen, in a kettle heated to 270°C and the melt is stirred for half an hour. It is then extruded through a spinneret under a nitrogen pressure of 5 atmospheres gauge and the cooled filament is wound up on a spinning bobbin. The filaments produced show an excellent brightening effect which is stable to thermofixing and has good fastness to washing and to light.

EXAMPLE 15

An intimate mixture of 100 parts of polyvinyl chloride, 3 parts of stabiliser (Advastat BD 100, Ba/Cd complex), 2 parts of titanium dioxide, 59 parts of dioctyl phthalate and 0.01 to 0.2 part of one of the compounds of the formulae (17) to (27), (29) to (33), (35), (38) or (39) is milled on a calender at 150° to 155°C to give a sheet. The opaque polyvinyl chloride sheet thus obtained has a substantially higher degree of whiteness than a sheet which does not contain the optical brightener.

EXAMPLE 16

100 parts of polystyrene and 0.1 part of one of the compounds of the formulae (17), (19), (20), (23), (25) and (31) are fused, with exclusion of air, for 20 minutes at 210°C in a tube of 1 cm diameter. After cooling, an optically brightened polystyrene composition of good fastness to light is obtained.

EXAMPLE 17

A 13% strength casting composition of acetylcellulose in acetone which contains — relative to dry weight of plastic — 2% of anatase (titanium dioxide) as a delustering agent, and 0.04% of a compound of the formulae (17) to (27), (29) to (33), (35), (38) or (39) is poured on a glass plate and spread with a metal rod to give a thin film. After drying, the film shows a substantially higher degree of whiteness than a film prepared in the same way, which does not contain an optical brightener.

EXAMPLE 18

7 g of anatase (TiO$_2$), followed by 350 g of acrylonitrile polymer in powder form, are added to 1,400 ml of dimethylformamide. The mixture is converted to a viscous mass by means of a high speed stirrer. 5 mg of the compound of the formulae (25), (31), (32) or (33) are dissolved in 50 g of this 20% strength polyacrylonitrile solution and after removing air bubbles the composition is cast on a glass plate and spread with a metal rod, with 1 mm thick stirrer sleeves, to give a uniform film. After drying in a stream of air, the film can be stripped off the glass plate. It has a substantially higher degree of whiteness than a film prepared in the same way, which does not contain the optical brightener.

What we claim is:

1. Compounds of the formula

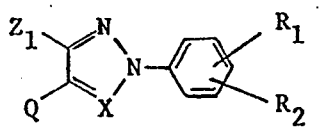

wherein $Z_1$ represents hydrogen or methyl, $R_1$ represents hydrogen, halogen, alkyl with 1 to 4 carbon atoms or alkoxy with 1 to 4 carbon atoms, $R_2$ represents hydrogen, halogen or alkyl with 1 to 4 carbon atoms, X represents nitrogen and Q represents a radical

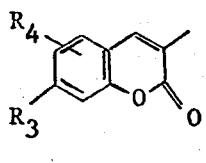

or

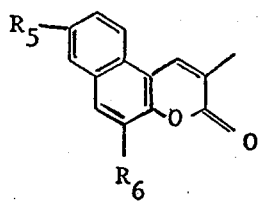

wherein $R_3$ denotes alkoxy with 1 to 12 carbon atoms, benzyloxy which is optionally chlorine-substituted in the phenyl radical, acetylamino, a —NHCOOY radical, wherein Y represents alkyl with 1 to 12 carbon atoms or phenyl which is optionally substituted by chlorine, methyl or methoxy, or phenyl which is optionally substituted by chlorine, methyl or methoxy, an optionally quaternised radical

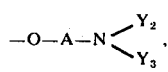

wherein A represents alkylene with 2 to 4 carbon atoms, $Y_2$ and $Y_3$ independently of one another represent optionally hydroxy-substituted alkyl with 1 to 4 carbon atoms, $R_4$ denotes hydrogen, chlorine, methyl or methoxy and $R_5$ and $R_6$ independently of one another denote hydrogen or alkyl with 1 to 4 carbon atoms.

2. Compounds according to claim 1, corresponding to the formula

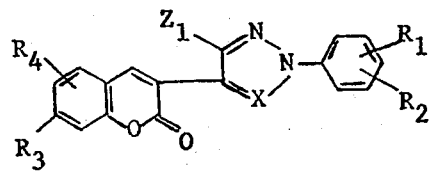

wherein $Z_1$, $R_1$, $R_3$, $R_4$ and X have the meaning indicated in claim 1.

3. Compounds according to claim 1, corresponding to the formula

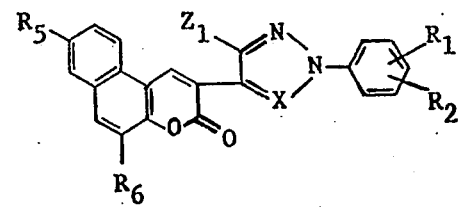

wherein $Z_1$, $R_1$, $R_2$, $R_5$, $R_6$ and X have the meaning indicated in claim 1.

4. Compounds according to claim 1, corresponding to the formula

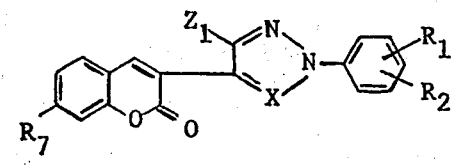

wherein $Z_1$ denotes hydrogen or methyl, $R_1$ denotes hydrogen, halogen, alkyl with 1 to 4 carbon atoms or alkoxy with 1 to 4 carbon atoms, $R_2$ denotes hydrogen, halogen or alkyl with 1 to 4 carbon atoms, $R_7$ denotes alkoxy with 1 to 12 carbon atoms or benzyloxy which is optionally chlorine-substituted in the phenyl part, and X denotes nitrogen.

5. Compounds according to claim 1, corresponding to the formula

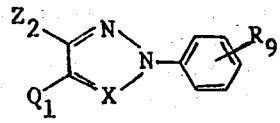

wherein $Z_2$ denotes hydrogen or methyl, $R_9$ denotes hydrogen, methyl or chlorine, X denotes nitrogen and $Q_1$ denotes a radical

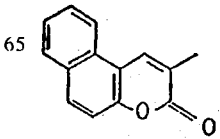

wherein $R_{11}$ represents alkoxy with 1 to 4 carbon atoms, benzyloxy, acetamido or a carbamic acid ethyl ester radical.

6. Compounds according to claim 5, corresponding to the formula

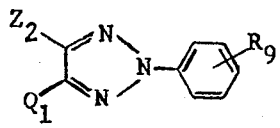

wherein $Z_2$, $R_9$ and $Q_1$ have the meaning indicated in claim 5.

7. Compounds according to claim 1, corresponding to the formula

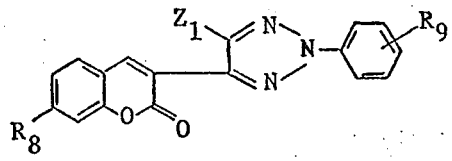

wherein $Z_1$ denotes hydrogen, chlorine or methyl, $R_8$ denotes alkoxy with 1 to 4 carbon atoms or benzyloxy and $R_9$ denotes hydrogen, chlorine or methyl.

8. Compounds according to claim 1, corresponding to the formula

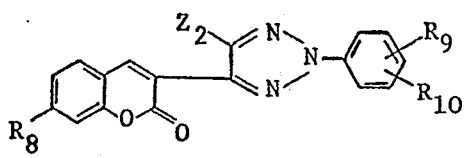

wherein $Z_2$ denotes hydrogen or methyl, $R_8$ denotes alkoxy with 1 to 4 carbon atoms or benzyloxy, $R_9$ denotes hydrogen, chlorine or methyl and $R_{10}$ denotes hydrogen, chlorine or methyl.

9. A compound of claim 1 having the formula

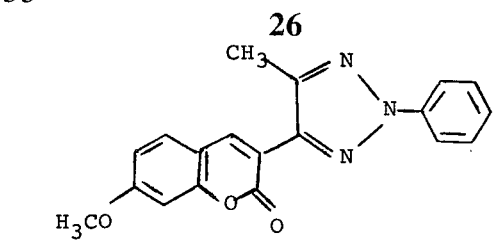

10. A compound of claim 1 having the formula

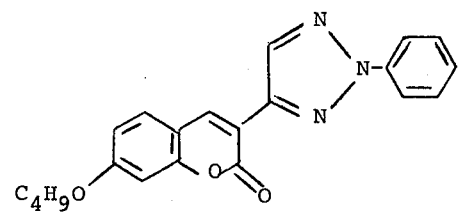

11. A compound of claim 1 having the formula

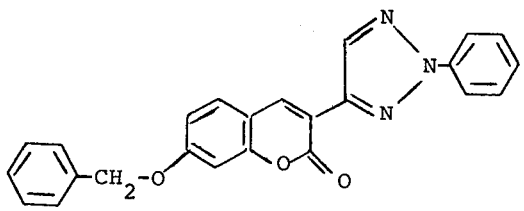

12. A compound of claim 1 having the formula

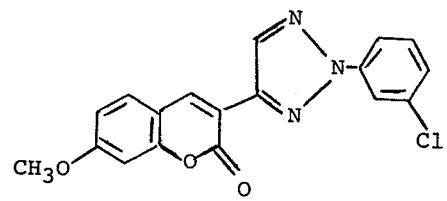

* * * * *

UNITED STATES PATENT AND TRADEMARK OFFICE
CERTIFICATE OF CORRECTION

PATENT NO. : 3,966,755
DATED : June 29, 1976
INVENTOR(S) : HANS SCHLÄPFER

It is certified that error appears in the above-identified patent and that said Letters Patent are hereby corrected as shown below:

Column 23, claim 1, lines 56-67, delete "or phenyl which is optionally substituted . . . hydroxy-substituted alkyl with 1 to 4 carbon atoms,".

Signed and Sealed this

Eleventh Day of January 1977

[SEAL]

Attest:

RUTH C. MASON
Attesting Officer

C. MARSHALL DANN
Commissioner of Patents and Trademarks